United States Patent [19]

Loscher et al.

[11] Patent Number: 4,466,429

[45] Date of Patent: Aug. 21, 1984

[54] APPARATUS FOR PRODUCING A CAVITY IN A BONE

[75] Inventors: Lothar W. Loscher, Munich; Frank Hoogeveen, Rohrmoos; Gerd Hanselmann, Dachau, all of Fed. Rep. of Germany

[73] Assignee: M.A.N. Maschinenfabrik Augsburg-Nurnberg AG, Munich, Fed. Rep. of Germany

[21] Appl. No.: 338,470

[22] Filed: Jan. 11, 1982

Related U.S. Application Data

[63] Continuation-in-part of Ser. No. 133,374, Mar. 24, 1980, abandoned.

[30] Foreign Application Priority Data

Apr. 10, 1979 [DE] Fed. Rep. of Germany ....... 2914455

[51] Int. Cl.$^3$ .......................... A61F 5/04; A61F 17/32
[52] U.S. Cl. .................................. 128/92 E; 128/305; 128/310
[58] Field of Search ............... 408/22, 24, 118; 128/317, 92 R, 92 E, 92 EB, 92 EC, 312, 315, 333, 305, 310

[56] References Cited

U.S. PATENT DOCUMENTS

| 505,712 | 9/1893 | Lofdahl | 408/22 |
|---|---|---|---|
| 816,277 | 3/1906 | Townley | 408/22 |
| 2,435,863 | 2/1948 | Wydro | 128/317 |
| 2,659,969 | 11/1953 | Merkur | 128/317 |
| 3,978,862 | 9/1976 | Morrison | 128/317 |
| 3,986,512 | 10/1976 | Walliser | 128/317 |
| 4,020,555 | 5/1977 | Hedrick | 128/317 |
| 4,124,026 | 11/1978 | Berner et al. | 128/92 E |
| 4,273,117 | 6/1981 | Neuhäuser | 128/92 E |
| 4,306,550 | 12/1981 | Forte | 128/92 E |

Primary Examiner—C. Fred Rosenbaum
Assistant Examiner—Michelle N. Lester
Attorney, Agent, or Firm—Alan H. Levine

[57] ABSTRACT

An apparatus comprising two rasping halves conforming generally to the shape of the bone cavity to be produced, and a drive mechanism for reciprocating both rasping halves counter to each other in an axial direction. A rotary cutting tool in front of the rasping halves prepares the bone cavity to receive the rasping halves. A flexible drive shaft for the cutting tool extends between the rasping halves and rotatably within a drive shaft for the rasping halves. The latter drive shaft has a slot oriented at an angle to the axis of rotation of the drive shaft, and a pin projects from each rasping half into the slot, the pins being located 180° apart. A bushing guides the movement of the rasping halves, and the pin from each rasping half extending through a slot in a housing for their drive shaft prevents twisting of the rasping halves.

12 Claims, 5 Drawing Figures

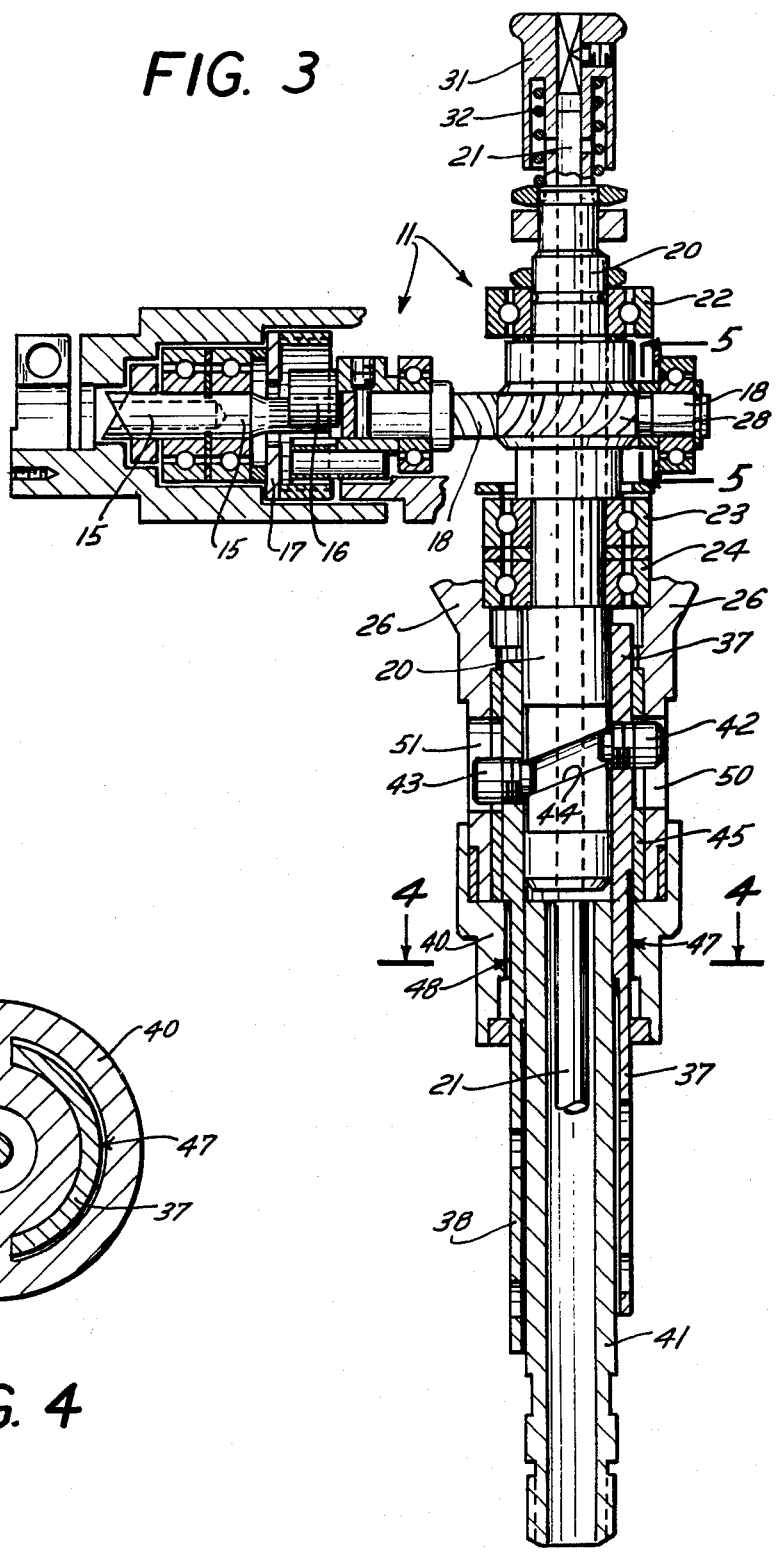

APPARATUS FOR PRODUCING A CAVITY IN A BONE

This is a continuation-in-part of our prior co-pending application Serial No. 06/133,374, filed Mar. 24, 1980, and now abandoned.

This invention relates to apparatus for producing a cavity in a bone for insertion of an artificial joint member. Such bone cavities are required, e.g., to incorporate the ball and shank portions of hip endoprotheses.

Such bone cavities have in the past been created manually; by means of scrapers and rasps, a cavity is formed in the bone especially after sawing off the upper end of a hip bone bearing the ball of the joint. A bone cavity formed in this way is inevitably inaccurate and, more importantly, considerably oversized. Once the bone cavity has been produced, it is filled with bone cement, after which the artificial joint member is inserted.

After the bone cement hardens, the artificial joint member is installed firmly in the bone, but with no play left. A considerable disadvantage of this known approach is that manual production of the bone cavity involves considerable effort. It requires considerable force and time (of about 30 minutes for each bone cavity to be formed), so that the total operating time is increased significantly. Another consideration is that the bone cement does not safely sustain high loads. Nor can the bone cement be prevented from crumbling in the course of time, leaving the artificial joint member fitting loosely in the bone. Once the artificial joint member loosens, re-operation becomes necessary.

It is a broad object of the present invention to provide a simple and effective apparatus to eliminate the disadvantage set forth above and, more particularly, to permit the formation of a bone cavity to accommodate an artificial joint member in a manner such that the bone cavity will provide an ideal fit with little effort and in a short period of time.

It is another object of the present invention to provide a machine-driven tool having two convex rasping halves corresponding to the shape of the bone cavity to be produced, both rasping halves slidingly touching each other at respective edges in a longitudinal plane, a drive mechanism being provided for reciprocating both rasping halves, one counter to the other.

In a preferred embodiment of the present invention, the apparatus presents in front of the rasping halves, viewed in the axial direction of feed, a conical drill bit or rotary cutter tool to prepare the bone cavity for insertion of the rasping halves. The rotary tool, i.e., drill bit or cutter, is attached at its rear end, viewed in the axial direction of feed, to a drive shaft arranged between the rasping halves. In an especially advantageous embodiment of the present invention, the rotary tool drive shaft is rotatably and flexibly arranged in a support adapted to the form of the bone cavity to be produced.

The apparatus of the present invention serves its purpose in a particularly simple manner. The two rasping halves can accurately be adapted to suit the form of the bone cavity to be produced, and, its drive can be controlled by machine with great accuracy so that the bone cavity provides a very good fit. Inasmuch as the rasping halves are driven by machine, the operator need use little force, and the time required to produce a bone cavity is shortened considerably. With the rotary tool preceding the rasping halves, the tool being one which answers the general description of a narrow cavity drill bit, the bone cavity is prepared in a simple fashion to accommodate the rasping halves. The rotary tool drive shaft, being flexible, readily adapts to any shape of bone cavity to be produced.

According to an advantageous feature of the present invention, the rasping halves are furnished with a drive mechanism in a tool housing arranged outside the bone cavity to be produced. According to another advantageous feature of the present invention, the drive mechanism for the rasping halves has a drive shaft which rotatably surrounds the rotary tool drive shaft, the former drive shaft having a circumferentially extending slot running at an angle to the axis of rotation of the shaft. A pin is attached to each rasping half, the two pins being spaced 180° apart and engaging in the circumferential slot such that when the rasping halves drive shaft rotates, the rasping halves are caused to reciprocate axially. In this simple way a kinetic connection is established between the rasping halves and their drive shaft such that when said drive shaft rotates, the rasping halves move through an axial stroke the length of which is determined by the angle of the circumferential slot.

According to another advantageous feature of the present invention, the rasping halves drive mechanism permits the rasping halves to slide in the axial direction of feed within a bushing or sleeve made of a bearing material, preferably bronze, and arranged between the tool housing and the rasping halves drive shaft. This provides for low-friction guidance of the two rasping halves especially in the axial direction.

According to a further advantageous feature of the present invention, the rasping halves drive mechanism has two pins each having an extended portion on the outer side of the rasping halves, the extended portions reaching through slots in the bushing and through corresponding slots in the tool housing. This feature provides, in a simple way, very satisfactory guidance for the rasping halves, and also prevents them from twisting in the circumferential direction of the tool.

According to another advantageous feature of the present invention, the flexible rotary tool drive shaft is held at its rear end, viewed in the axial direction of feed, in a rotary chuck preferably arranged behind the drive mechanism for the rasping halves, viewed in the axial direction of feed. This provides a simple drive arrangement for the rotary tool drive shaft and holds the flexible drive shaft in his position by tensioning the drive shaft in the rear direction by means of a spring.

According to a further advantageous feature of the present invention, a worm drive driven by a planetary gearset is provided to operate the rasping halves drive shaft.

The transmission of rotational movement to the apparatus can be achieved via flexible shafts by means of surgical motors. The apparatus can advantageously be operated also on compressed air.

The feed movement of the tool to suit the intended shape of the bone cavity can be effected in such a way that the progress of the work can be observed on a monitor and the tool manually guided accordingly.

The invention will now be described more fully with reference to the accompanying drawings, illustrating a preferred embodiment, in which:

FIG. 3 is a detail view, of a portion of FIG. 1, in longitudinal cross-section, with parts broken away;

FIG. 4 is a cross-sectional view taken along line 4—4 of FIG. 3; and

Figure 1:
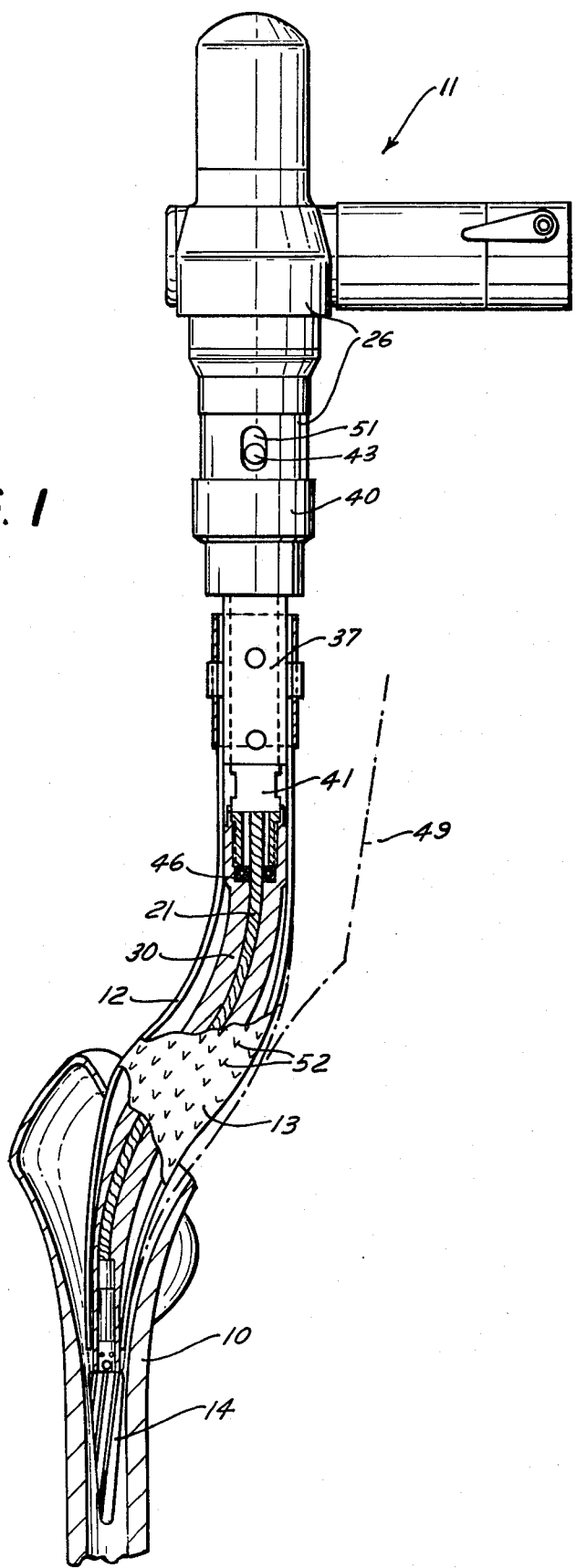
FIG. 1 is an elevational view, partially in longitudinal cross-section with housing portions broken way, of an apparatus for producing a bone cavity.

The apparatus shown in FIG. 1 serves to produce a cavity in a bone 10 to permit insertion of an artificial joint member. The apparatus is a machine-driven tool having a drive mechanism 11, two rasping halves 12 and 13 and in front of the rasping halves 12 and 13, viewed in the axial feed direction, a rotary cutting tool 14.

The drive mechanism 11, more clearly shown in FIG. 3, comprises a first flexible drive shaft 15 arranged for rotary movement and rotary driven by means of a surgical motor (not shown). The rotating speed of the flexible drive shaft 15 is reduced through a planetary gearset 16. The movement of the gearset 16 is transmitted through a cage 17 to a worm shaft 18.

Figure 5:
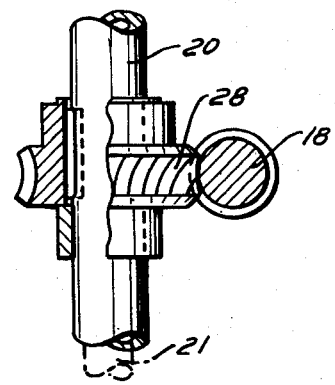
FIG. 5 is a view of a gear means, with parts broken away.

The drive mechanism 11 including a drive shaft 20 surrounding a flexible rotary drive shaft 21 is supported with bearings 22 to 24 in a tool housing 26. The drive shaft 20 ends in a worm shaft 18 cooperating with a worm wheel 28 to form a worm gear, more clearly shown in FIG. 5, for imparting the rotary movement to the tool drive shaft 21.

The rotary tool drive shaft 21 is arranged for rotary movement within a stiff support 30 shaped to fit the form of bone cavity to be produced. At its rear end, viewed in the axial direction of feed, the rotary tool shaft 21 is provided with a rotary chuck 31. A spring 32 is pressed between said rotary chuck 31 attached to the rotary tool shaft 21 and a ring 32 attached to the drive shaft 20 for holding the rotary tool shaft in tension. To the other end of the rotary tool drive shaft 21 is attached the rotary tool 14 of a type known for surgical operations and having the shape of a conical drill bit (marrow cavity drill). The rotary tool 14 is made of Steel and prepares the bone cavity for insertion of the rasping halves 12 and 13.

Figure 2:
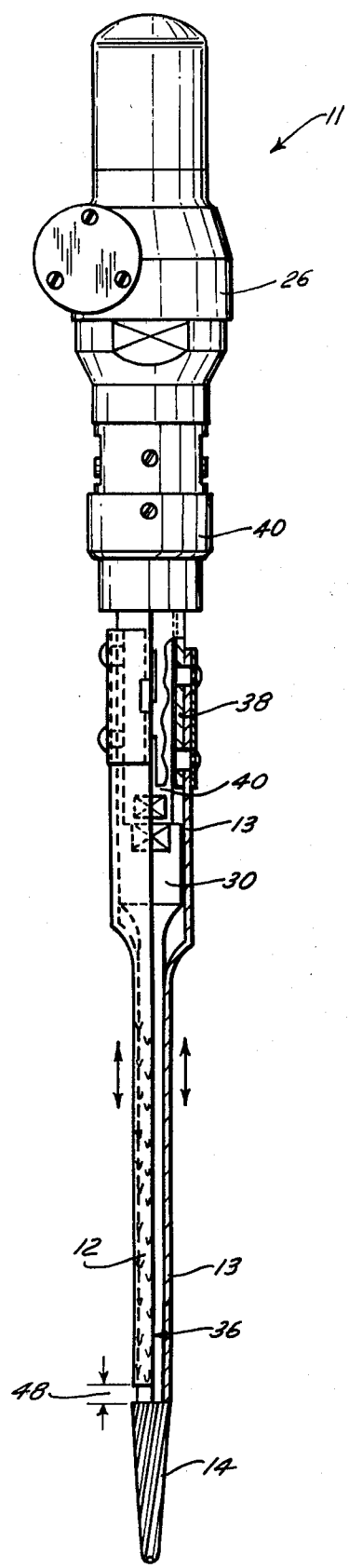
FIG. 2 is an elevational view, partially in longitudinal cross-section, turned 90° with respect to FIG. 1.

The rasping halves 12 and 13 are formed to suit the shape of the bone cavity to be produced. Each half is convex so as to form a tubular structure with different cross sections along the axis when both halves are put together. This tubular structure and hence each rasping half have in one plane a curved form for instance like an open "S" as shown in FIG. 1 while they are straight in a perpendicular plane, as shown in FIG. 2. The curved form and the cross-section may change in accordance to the bone to be treated. The cross-section therefore can be of triangular, oval, or circular form. The rasping halves face each other at a plane 36 being capable of sliding against each other when axially relatively moved one counter to the other. The relative movement one counter the other does not necessarily imply that one rasping half is fixed while the other is movable; rather, in practice, the only arrangement which is important is one in which the two rasping halves 12 and 13 both move, one with respect to the other.

The rasping halves 12 and 13 are refined steel casting or made of refined steel sheet having rough rasp teeth 52 as used in surgical tools or for rasps for rasping wood or used in the kitchen.

The rasping halves 12 and 13 surround the stiff support 30 leaving enough space between the support 30 and the rasping halves 12 and 13 for relative axial movement. The rasping halves 12 and 13 are screwed to respective shell halves 37 and 38. The shell halves are being supported for sliding movement between the lower end of the drive shaft 20 and a bronze bushing 45 and in respective slots 47 and 48 of a socket 40.

The shell halves 37 and 38 are each provided with respective pins 42, 43, engaging in a circumferentially extending slot 44 provided in the drive shaft 20. The pins being spaced 180° apart have a portion extending through the bushing 45 into respective slots 50, 51 provided in the housing 26. The guidance of the shell halves 37 and 38 in respective slots 47, 48 of the socket 40 and of the pins 42 and 43 in respective slots 50, 51 of the housing 26 serve to prevent twisting of the shell halves 37 and 38 and the rasping halves 12 and 13. The circumferentially extending slot 44 runs at an angle to the axis of rotation of the shaft 20 for forcing the pins 42, 43 to move up and down when the drive shaft 20 is rotated.

The socket 40 has a cylindrical extension 41 for connecting the stiff support 30 through the socket 40 to the housing 26. A bearing 46 attached to the end of the cylindrical extension 41 serves for frictionless guiding of the flexible tool shaft 21 into the stiff support 30.

As a result, when the drive shaft 20 rotates, the flexible tool shaft is caused to rotate while the rasping halves 12 and 13 are caused through the circumferentially extending slot 44 the pins 42 and 43 and the shell halves 37 and 38 to reciprocate axially. The axial stroke 48 experienced by the rasping halves 12 and 13 in the process is about 0.2 to 0.4 inches (5 to 10 mm). The rotary velocity of the drive shaft 20 and consequently of the flexible drive shaft 21 and the rotary tool 14 can be continuously raised from 0 to 900 Rpm. In each revolution the rasping halves move one time up and down, that is they move from 0 to 360 or 720 in/Min depending on the stroke. In operation the apparatus is manually guided. While the rotary tool 14 prepares the cavity for insertion of the rasping halves 12 and 13 the rasping halves remove by their reciprocating axial movement the bone substance of bone 10. This operation is done in a short time, requiring but little effort from the operator. Furthermore, the rasping halves operate with an accuracy such that an ideally mating bone cavity is produced to accommodate the artificial joint member to be inserted.

The direction of insertion of the tool into the bone 10 is characterized by the bent line 49. The tool can be made to follow this line 49 in such a way that the progress of the work can be observed on a monitor and the tool manually guided in a suitable manner.

The invention has been shown and described in preferred form only, and by way of example, and many variation may be made in the invention which will still be comprised within its spirit. It is understood, therefore, that the invention is not limited to any specific form or embodiment exept insofar as such limited to any specific form or embodiment except insofar as such limitations are included in the appended claims.

We claim:

1. Apparatus for producing a cavity in a bone to accommodate an artificial joint member, comprising two longitudinally extending rasping halves each said half having, in cross-section, a relatively broad outer surface portion extending between two inwardly directed, relatively narrow, edge portions, the corresponding edge portions of said rasping halves being disposed adjacent to each other so that said halves, together, conform generally to the shape of the bone cavity to be produced, said halves further including cutting teeth on the outer surfaces thereof; and, means for reciprocating both rasping halves, in a substantially axial direction, such that the rasping halves move counter to each other.

2. Apparatus for producing a cavity in a bone as defined in claim 1 wherein said rasping halves are convex and are in sliding contact at an axial plane to form a hollow body with a non-constant cross section along its axis.

3. Apparatus for producing a cavity in a bone as defined in claim 1 further including a rotary cutting tool in front the rasping halves for preparing the bone cavity to receive the rasping halves.

4. Apparatus for producing a cavity in a bone as defined in claim 3 further including a drive shaft for rotating the cutting tool, the drive shaft extending between the rasping halves.

5. Apparatus for producing a cavity in a bone as defined in claim 4 wherein the drive shaft is flexible, and said apparatus further including a support for the drive shaft, the support generally conforming to the shape of the cavity to be produced.

6. Apparatus for producing a cavity in a bone as defined in claim 1 wherein the means for reciprocating the rasping halves are within a housing located outside the cavity to be produced.

7. Apparatus for producing a cavity in a bone as defined in claim 1 wherein the means for reciprocating the rasping halves includes a rotatable drive shaft having a slot oriented at an angle to the axis of rotation of the drive shaft, and including a pin projecting from each rasping half into the slot, the pins being spaced 180° apart around the periphery of the drive shaft, whereby rotation of the drive shaft produces reciprocation of the rasping halves.

8. Apparatus for producing a cavity in a bone as defined in claim 7 further including a rotary cutting tool in front of the rasping halves, and a drive shaft for rotating the cutting tool, the cutting tool driving shaft extending rotatably within the drive shaft for the rasping halves.

9. Apparatus for producing a cavity in a bone as defined in claim 7 further including a housing enclosing the drive shaft for the rasping halves, and a bushing between the drive shaft and the housing, each rasping half being slidably guided within the bushing.

10. Apparatus for producing a cavity in a bone as defined in claim 7 further including a housing enclosing the drive shaft the housing having two slots, and each pin having a portion extending into a housing slot to prevent twisting of the rasping halves in the circumferential direction of the tool.

11. Apparatus for producing a cavity in a bone as defined in claim 8 further including a rotary chuck grasping the rear end of the rotary tool drive shaft, the chuck being behind the means for reciprocating the rasping halves.

12. Apparatus for producing a cavity in a bone as defined in claim 1 wherein the means for reciprocating the rasping halves includes a drive shaft, a worm and worm wheel for rotating the drive shaft, and a planetary gearset for rotating the worm and worm wheel.

* * * * *